(12) United States Patent
Stack et al.

(10) Patent No.: US 7,354,454 B2
(45) Date of Patent: Apr. 8, 2008

(54) SATIATION DEVICES AND METHODS

(75) Inventors: Richard S. Stack, Chapel Hill, NC (US); Richard A. Glenn, Chapel Hill, NC (US); Trevor J. Moody, Seattle, WA (US); Fred E. Silverstein, Seattle, WA (US); Nathan Every, Seattle, WA (US); William S. Eubanks, Jr., Durham, NC (US)

(73) Assignee: Synecor, LLC, Durham, NC (US)

( * ) Notice: Subject to any disclaimer, the term of this patent is extended or adjusted under 35 U.S.C. 154(b) by 428 days.

(21) Appl. No.: 10/892,973

(22) Filed: Jul. 16, 2004

(65) Prior Publication Data

US 2005/0004681 A1     Jan. 6, 2005

Related U.S. Application Data

(60) Continuation of application No. 10/457,108, filed on Jun. 9, 2003, now Pat. No. 7,111,627, which is a division of application No. 09/940,110, filed on Aug. 27, 2001, now Pat. No. 6,675,809.

(51) Int. Cl.
*A61F 2/04* (2006.01)

(52) U.S. Cl. .................. 623/23.65; 623/7; 600/37; 604/7; 604/8; 604/264

(58) Field of Classification Search ............ 623/23.65, 623/23.67, 23.68, 23.7
See application file for complete search history.

(56) References Cited

U.S. PATENT DOCUMENTS

| | | | |
|---|---|---|---|
| 4,246,893 A | 1/1981 | Berson | 128/898 |
| 4,315,509 A | 2/1982 | Smit | 606/108 |
| 4,403,604 A | 9/1983 | Wilkinson et al. | 600/37 |
| 4,416,267 A | 11/1983 | Garren et al. | 128/898 |
| 4,441,215 A | 4/1984 | Kaster | 623/1.53 |
| 4,607,618 A | 8/1986 | Angelchik | 128/898 |
| 4,641,653 A | 2/1987 | Rockey | 606/194 |
| 4,648,383 A | 3/1987 | Angelchik | 128/899 |
| 4,694,827 A | 9/1987 | Weiner et al. | 606/192 |
| 4,723,547 A | 2/1988 | Kullas et al. | 606/185 |
| 4,846,836 A | 7/1989 | Reich | 623/11 |
| 4,899,747 A | 2/1990 | Garren et al. | 606/192 |
| 5,163,952 A | 11/1992 | Froix | 623/1.18 |
| 5,211,658 A | 5/1993 | Clouse | 623/1.14 |
| 5,234,454 A | 8/1993 | Bangs | 606/191 |

(Continued)

FOREIGN PATENT DOCUMENTS

EP     0 775471 A1     5/1997

(Continued)

*Primary Examiner*—Corrine McDermott
*Assistant Examiner*—Javier C. Blanco
(74) *Attorney, Agent, or Firm*—Stallman & Pollock LLP

(57) ABSTRACT

A device for inducing weight loss in a patient includes a tubular prosthesis self-expandable from a collapsed position in which the prosthesis has a first diameter to an expanded position in which the prosthesis has a second, larger, diameter. In a method for inducing weight loss, the prosthesis is placed in the collapsed position and inserted into a stomach of a patient. The prosthesis is allowed to self-expand from the collapsed position to the expanded position and into contact with the walls of the stomach, where it induces feelings of satiety and/or inhibits modulation of satiety-controlling factors such as Ghrelin.

14 Claims, 19 Drawing Sheets

U.S. PATENT DOCUMENTS

| | | | |
|---|---|---|---|
| 5,246,456 A | 9/1993 | Wilkinson | 623/23.65 |
| 5,259,399 A | 11/1993 | Brown | 128/897 |
| 5,290,217 A | 3/1994 | Campos | 600/37 |
| 5,306,300 A | 4/1994 | Berry | 623/23.64 |
| 5,314,473 A | 5/1994 | Godin | 623/12 |
| 5,327,914 A | 7/1994 | Shlain | 128/898 |
| 5,345,949 A | 9/1994 | Shlain | 128/898 |
| 5,405,377 A | 4/1995 | Cragg | 623/1.2 |
| 5,514,176 A | 5/1996 | Bosley, Jr. | 623/1.15 |
| 5,593,434 A | 1/1997 | Williams | 128/898 |
| 5,653,743 A | 8/1997 | Martin | 623/1.35 |
| 5,662,713 A | 9/1997 | Andersen et al. | 128/898 |
| 5,674,241 A | 10/1997 | Bley et al. | 623/1.2 |
| 5,709,657 A | 1/1998 | Zimmon | 604/101.05 |
| 5,720,776 A | 2/1998 | Chuter et al. | 623/1.36 |
| 5,749,918 A | 5/1998 | Hogendijk et al. | 623/1.14 |
| 5,771,903 A | 6/1998 | Jakobsson | 128/898 |
| 5,820,584 A | 10/1998 | Crabb | 604/500 |
| 5,861,036 A | 1/1999 | Godin | 623/12 |
| 5,868,141 A | 2/1999 | Ellias | 128/898 |
| 5,887,594 A | 3/1999 | LoCicero, III | 128/898 |
| 5,922,019 A | 7/1999 | Hankh et al. | 623/1.13 |
| 5,993,483 A | 11/1999 | Gianotti | 623/1.22 |
| 6,102,922 A | 8/2000 | Jakobsson et al. | 606/157 |
| 6,113,609 A | 9/2000 | Adams | 606/139 |
| 6,146,416 A | 11/2000 | Andersen et al. | 623/1.15 |
| 6,159,238 A | 12/2000 | Killion et al. | 623/1.11 |
| 6,254,642 B1 | 7/2001 | Taylor | 623/23.64 |
| 6,258,120 B1 | 7/2001 | McKenzie et al. | 623/1.36 |
| 6,264,700 B1 | 7/2001 | Kilcoyne et al. | 623/1.68 |
| 6,302,917 B1 | 10/2001 | Dua et al. | 623/23.68 |
| 6,503,264 B1 | 1/2003 | Birk | 606/191 |
| 6,540,789 B1 | 4/2003 | Silverman et al. | 623/23.65 |
| 6,547,801 B1 | 4/2003 | Dargent et al. | 606/157 |
| 6,558,400 B2 | 5/2003 | Deem et al. | 606/151 |
| 6,572,627 B2 | 6/2003 | Gabbay | 606/151 |
| 6,575,896 B2 | 6/2003 | Silverman et al. | 600/29 |
| 6,596,023 B1 | 7/2003 | Nunez et al. | 623/1.3 |
| 6,663,639 B1 | 12/2003 | Laufer et al. | 606/139 |
| 6,740,121 B2 | 5/2004 | Geitz | 623/23.7 |
| 6,764,518 B2 | 7/2004 | Godin | 623/23.68 |
| 2001/0011543 A1 | 8/2001 | Forsell | 128/899 |
| 2001/0020189 A1 | 9/2001 | Taylor | 623/23.68 |
| 2001/0020190 A1 | 9/2001 | Taylor | 623/23.68 |
| 2002/0022851 A1 | 2/2002 | Kalloo et al. | 606/151 |
| 2002/0055757 A1 | 5/2002 | Torre et al. | 606/191 |
| 2002/0099439 A1 | 7/2002 | Schwartz et al. | |
| 2004/0092892 A1 | 5/2004 | Kagan et al. | 604/264 |
| 2004/0107004 A1 | 6/2004 | Levine et al. | 623/23.64 |

FOREIGN PATENT DOCUMENTS

| | | |
|---|---|---|
| WO | WO 91/01117 | 2/1991 |
| WO | WO 00/12027 | 3/2000 |
| WO | WO 00/32137 | 6/2000 |
| WO | WO 01/49359 | 7/2001 |
| WO | WO 03/094784 A2 | 11/2003 |

SATIATION DEVICES AND METHODS

PRIORITY

The present application is a continuation of U.S. patent application Ser. No. 10/457,108, filed Jun. 9, 2003 now U.S. Pat. No. 7,111,627, which is a divisional of U.S. patent application Ser. No. 09/940,110, filed Aug. 27, 2001 now U.S. Pat. No. 6,675,809.

FIELD OF THE INVENTION

The present invention relates generally to the field of devices and methods for achieving weight loss in humans, and specifically to the use of devices implantable within the human stomach for controlling feelings of hunger.

BACKGROUND OF THE INVENTION

Various medical approaches are used for controlling obesity. These approaches include diet, medication, and surgical procedures. One of the more successful surgical procedures is the vertical banded gastroplexy or the proximal gastric pouch with a Roux-en-Y anastomosis. However, known complications are present with each of these procedures and more successful options are desired.

Other alternatives include implantation of gastric balloons that prevent overeating by occupying volume within the stomach. Unfortunately, gastric balloons can migrate down the GI tract, causing obstruction and thus necessitating removal.

It is therefore desirable to provide a successful and minimally-invasive alternative to existing approaches for controlling obesity.

SUMMARY OF THE INVENTION

A satiation device utilizing principles of the present invention includes a tube having a collapsed position proportioned to permit introduction of the tube into a portion of the stomach. Once positioned within the body, the tube self-expands into contact with the interior of the stomach. During use, food ingested into the stomach passes through the tube. In an alternate embodiment, the tube may be formed of a material that prevents food within the tube from contacting the surrounding walls of the stomach. In one embodiment, the tube may be positionable within the antrum of the stomach. In other alternative embodiments, the device may include a fundal basket which may or may not be attached to a proximal end of an antral tube, and/or a bowel tube which may or may not be attached to a distal end of an antral tube.

In other alternative embodiments, a small pouch is attached to a cage structure such as a fundal basket and positioned at the proximal end of the stomach. In other alternative embodiments, this pouch may be provided without a cage structure and is independently secured against the proximal stomach wall by endoscopy guided sutures or other means.

DETAILED DESCRIPTION

Figure 1:
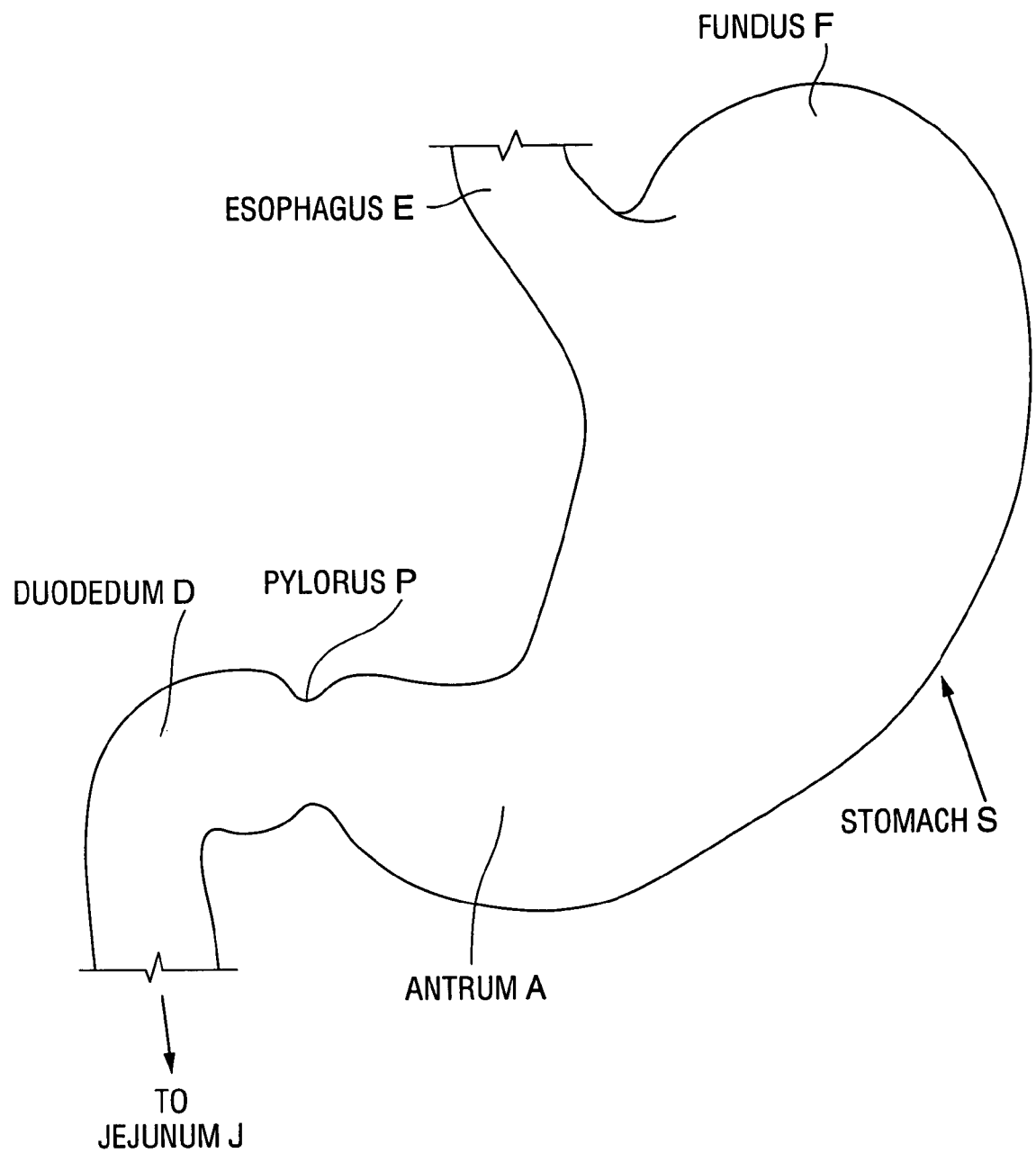
FIG. 1 is a schematic illustration of a human stomach and a portion of the small intestine.

An anatomical view of a human stomach S and associated features is shown in FIG. 1. Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

Various embodiments of satiation devices are described herein. Many of these devices include an antral tube positionable within the antrum A, and may optionally include a fundal tube connected to the proximal end of the antral tube for placement in the fundus F, and/or a bowel tube connected to the distal end of the antral tube for placement in the duodenum D.

The device may be modular in that that the various components may be provided separate from one another. In such a modular system, the separate implanted components may be attached to one another within the body during implantation, or certain ones of them may remain unattached to one another even after implantation. Alternatively, the physician may assemble the components to one another just prior to implantation. Modular components are desirable in that they permit the physician to select sizes for each component that are appropriate for the patient. As another alternative, the device may be a unitary device in the sense that the components (e.g. the antral tube, bowel tube and/or fundal basket) are not separately provided but instead form a single-unit implant.

Figure 2:
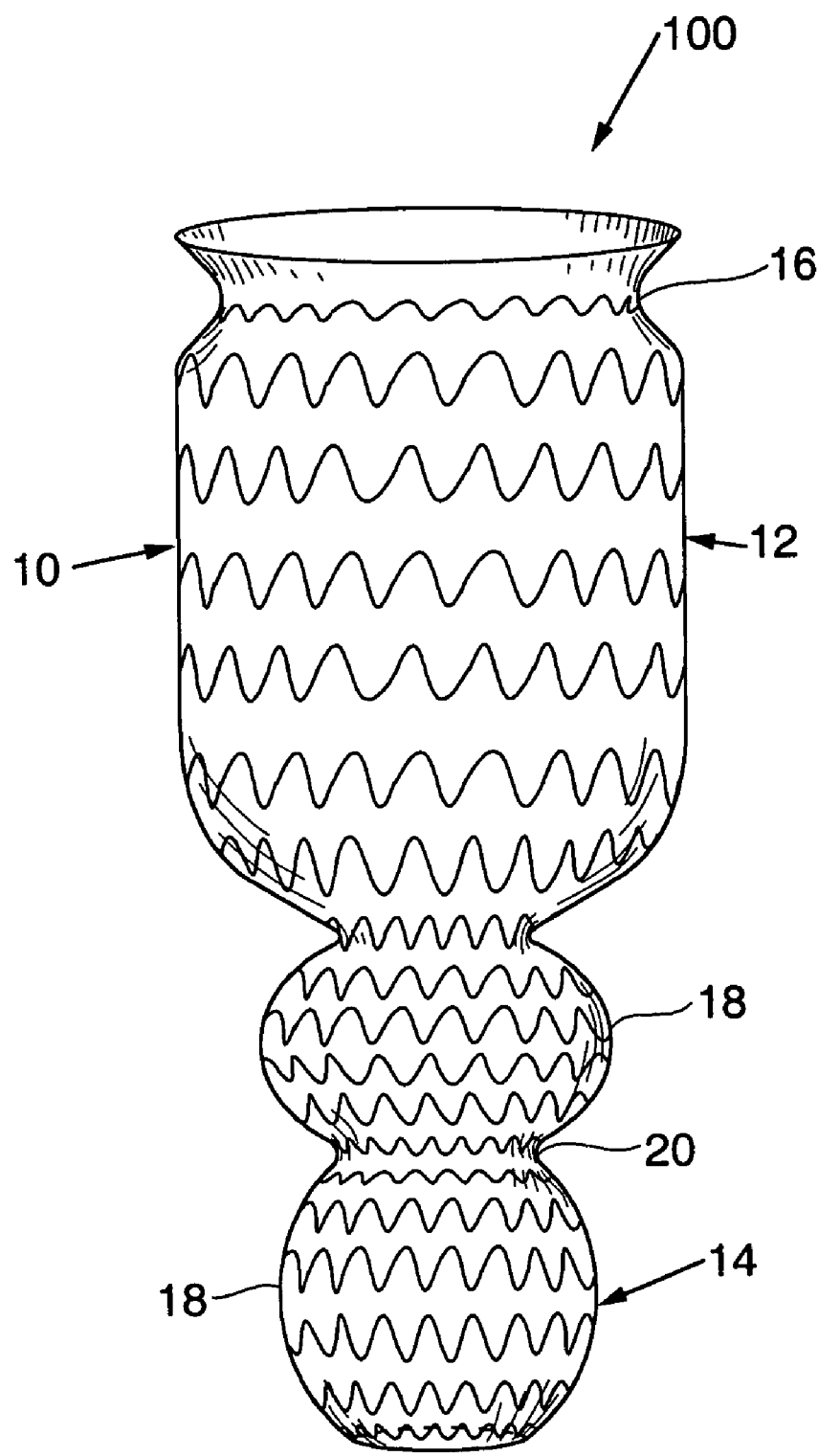
FIG. 2 is a plan view of a satiation device utilizing principles of the present invention.

FIG. 2 shows a first embodiment of a satiation device 100 utilizing principles of the present invention. Satiation device 100 includes an elongate tubular body 10 having a proximal section 12 and a distal section 14. Proximal section 12 includes a reduced diameter neck 16. Distal section 14 preferably has an hourglass profile including a pair of broadened sections 18 and a waisted section 20 between the broadened sections.

Tubular body 10 is proportioned to be at least partially positioned within the antrum of the stomach such that food moving into the antrum passes through the hollow interior of the tubular body. The tubular body 10 (which will also be referred to as the antral tube) may be made of shape memory materials such as nitinol or other shape memory alloys, or shape memory polymers, and is preferably made of a soft mesh or other framework formed of nitinol or stainless steel wires in combination with a polymeric barrier that prevents ingested food passing through the antral tube 10 from contacting the walls of the antrum. Thus, the polymeric barrier may be a skin formed on the exterior or interior of the mesh, or the mesh may be encapsulated in polymeric material or the polymer may be disposed in the interstices of the mesh. By preventing food from contacting the antrum walls as it passes from mid-stomach to the pylorus, the device prevents modulation of Ghrelin or other satiety controlling factors.

Figure 3:
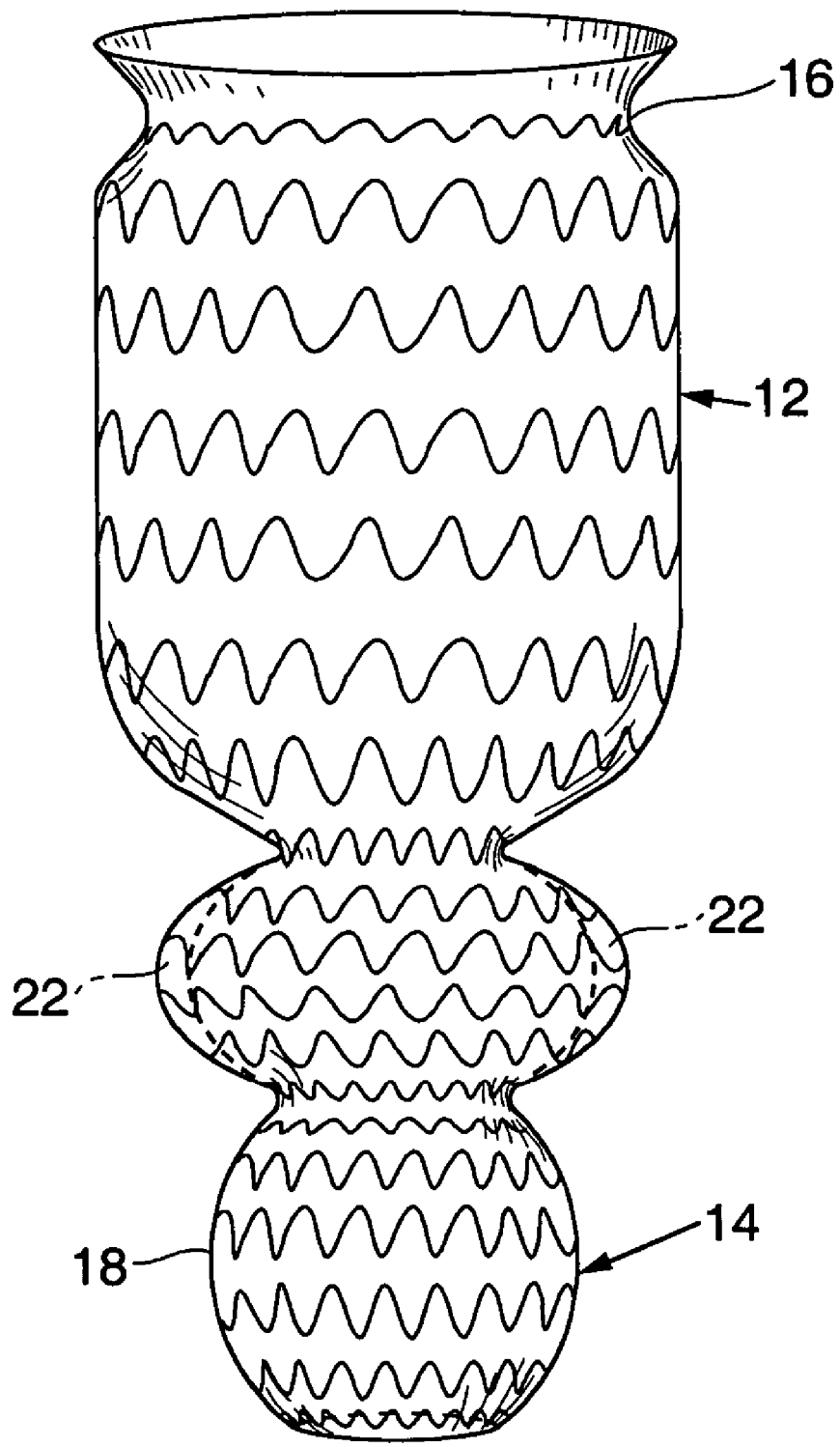
FIG. 3 is a plan view of a satiation device similar to that of FIG. 2, but including a drug delivery reservoir.

As shown in FIG. 3, the device 100 may optionally include one or more pharmaceutical delivery reservoirs 22, which are filled with substances known to inhibit release of Ghrelin or other hormones associated with feelings of satiety. Such substances may be chemical or pharmaceutical substances, therapeutic molecules or cells, or genetic material. Each such reservoir 22 may comprise a fluid pocket formed between a first layer of fluid impermeable polymeric material and a second layer of semi-permeable membrane that allows the substances to pass from the reservoirs into the surrounding tissue. Alternatively, the polymeric material used to form the tube may be impregnated with substances useful for maintaining low Ghrelin levels.

The reservoir or material containing the inhibitive substances may be in a portion of the device that lies within the antrum and/or in a portion that lies within the duodenum, particularly the segment of the duodenum that is proximal of the ampulla of vader, as it is believed that receptors for such substances are present in these areas.

During implantation, the antral tube 10 is passed into the patient blindly, under radiologic guidance, or under endoscopic guidance. Prior to implantation, the antral tube 10 is preferably packaged in a tubular sheath 26 (see FIG. 4A) by compressing the antral tube 10 about its longitudinal axis and inserting it into tubular sheath 26.

Figure 4A:
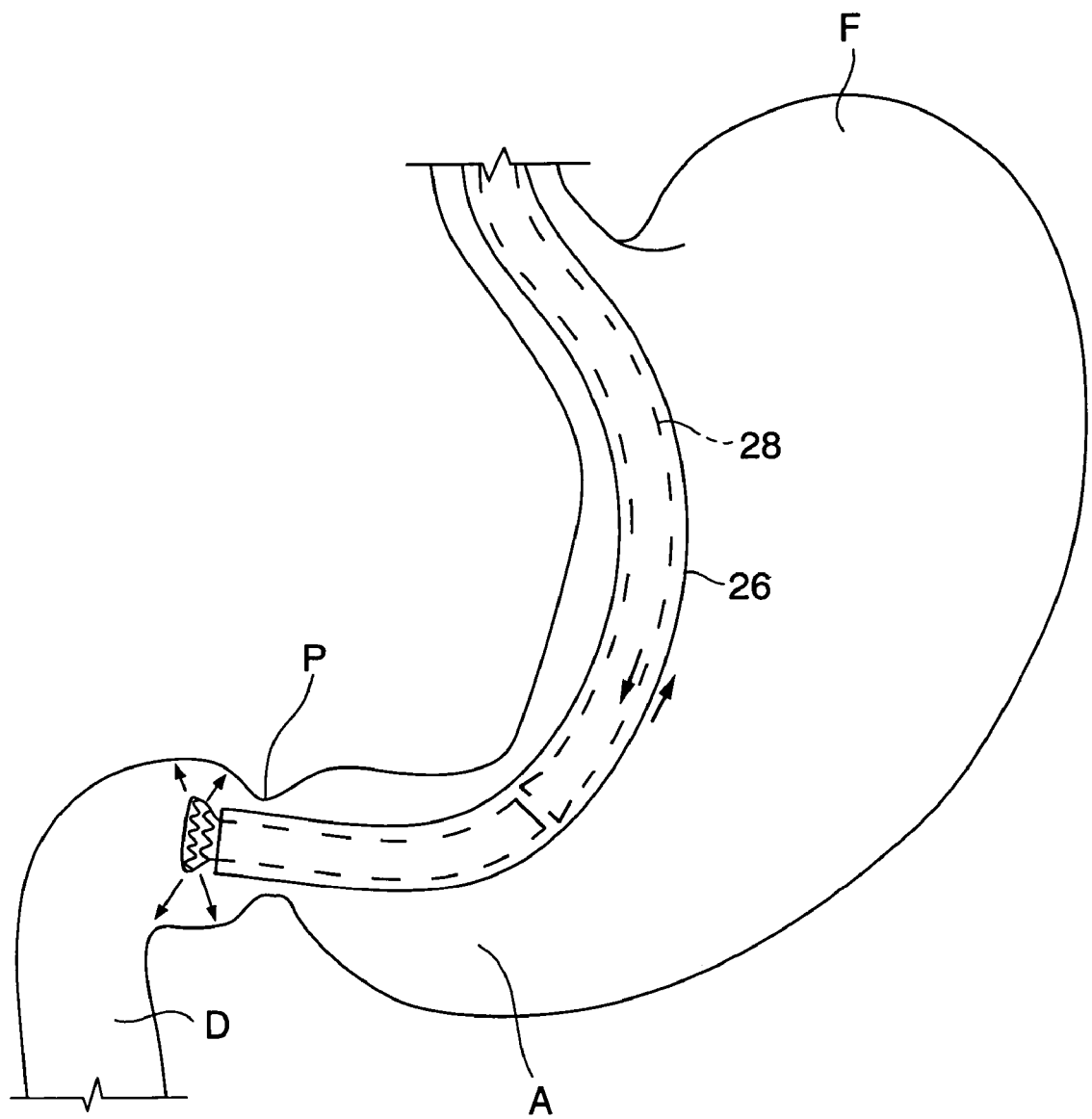
FIG. 4A is a schematic illustration of a stomach, pylorus, and bowel, showing introduction of the device of FIG. 2 or 3 into the antrum.

The sheath 26, with the antral tube 10 packaged inside, is passed into the stomach via the patient's mouth and positioned within the antrum as shown in FIG. 4A. The antral tube 10 is then pushed out the distal end of the sheath 26 using a pushing device 28 inserted into the proximal end of the sheath. The mesh forming the antral tube is preferably constructed so as to be self-expanding, such that the tube 10 springs radially open into an expanded condition upon its ejection from the sheath 26. When in its expanded condition, the antral tube exerts pressure against the interior surfaces against which it is in contact, so as to create the feeling of satiety and to inhibit Ghrelin release. The radial pressure of the device against the walls also secures the device against the walls of the antrum and prevents it from moving through the pylorus, even in the presence of peristalsis. In an alternative embodiment, the antral section is covered, such as by a polymeric material, shielding the stomach contents from the antrum. This may suppress chemical mediators of the sensation of hunger, such as grhelin production.

Figure 4B:
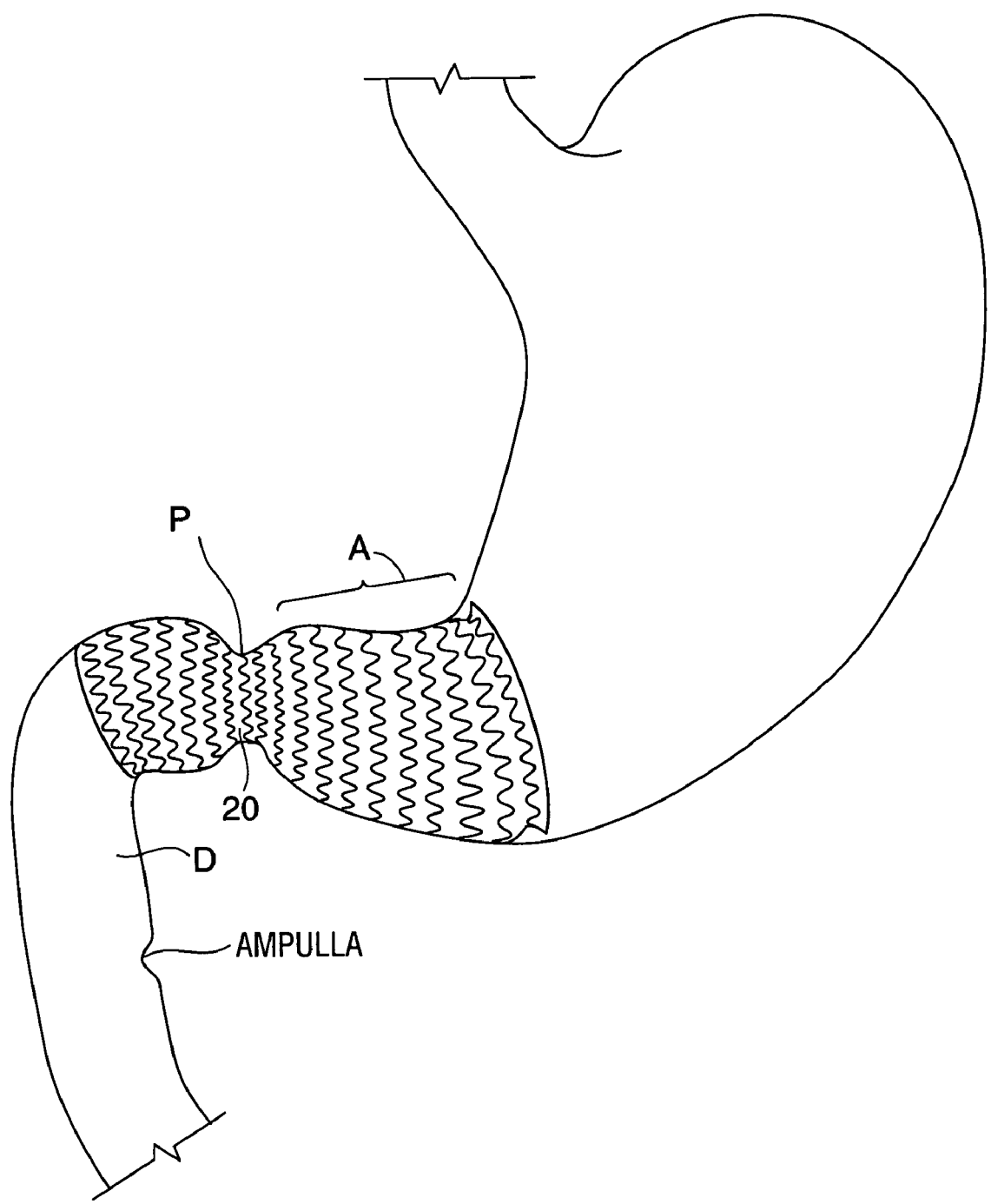
FIG. 4B is a schematic illustration similar to FIG. 4A, showing the device in position.

The hour-glass shape of the distal portion 14 is configured such that when the device is implanted, the waist section 20 becomes seated at the pyloric sphincter as shown in FIG. 4B. The helps to prevent migration of the device within the stomach, yet because of the self-expanding nature will avoid obstruction of the pylorus. It may be additionally desirable to provide the antral tube to include a valve (not shown) within the waist section 20, so as to prevent reflux of bile from the duodenum into the antrum.

Figure 4C:
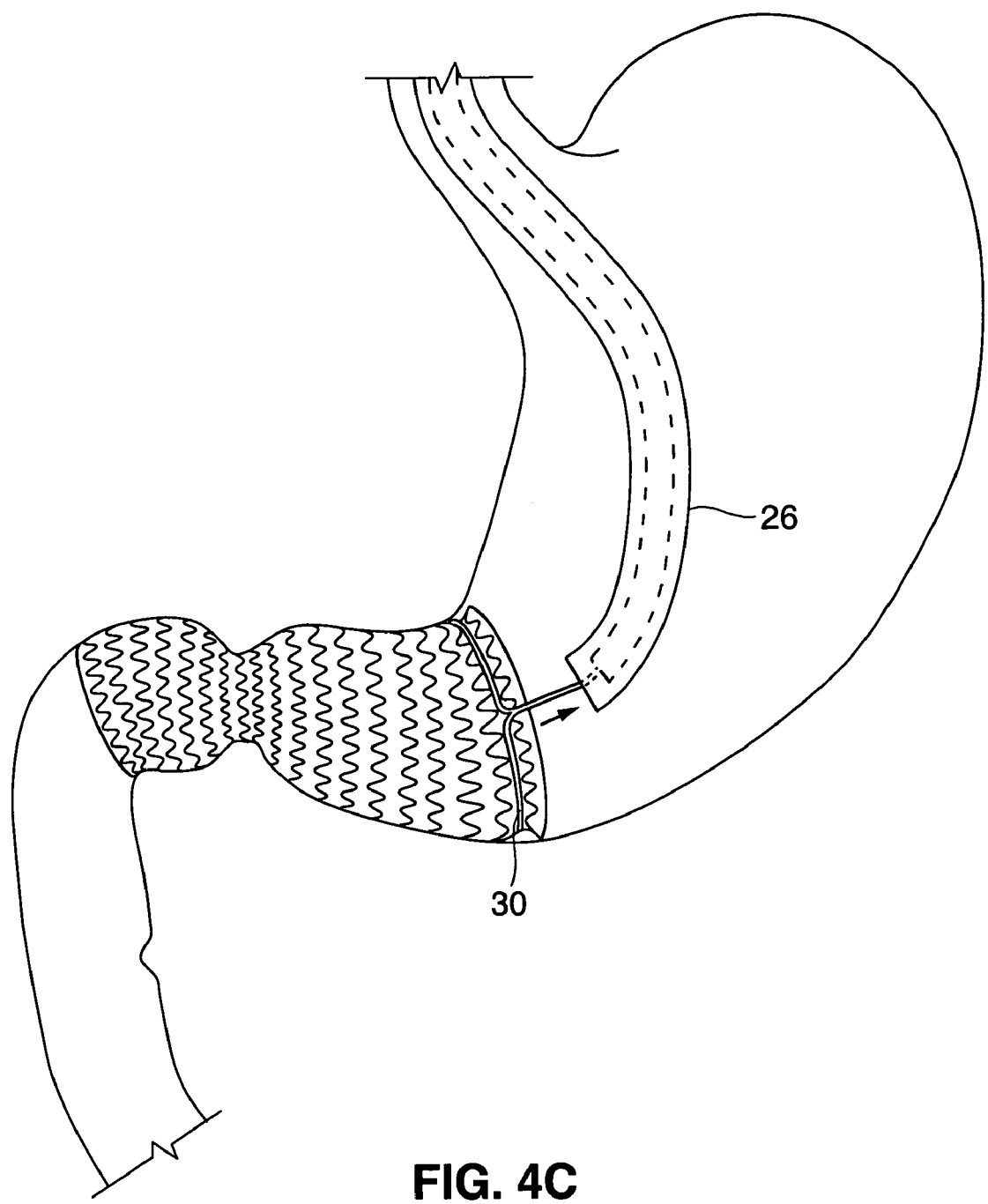
FIG. 4C is a schematic illustration similar to FIG. 4B, showing withdrawal of the device into a sheath for subsequent removal from the body.

Referring to FIG. 4C, removal of the device is carried out by inserting sheath 26 into the stomach, and by extending a grasping instrument such as snare 30 through the sheath. Snare 30 is closed around the neck 16 of the tube 10 and withdrawn, causing the tube 10 to collapse and be drawn into the sheath 26. Once the tube 10 is stored within the sheath, the sheath is withdrawn from the patient.

Figure 16A:
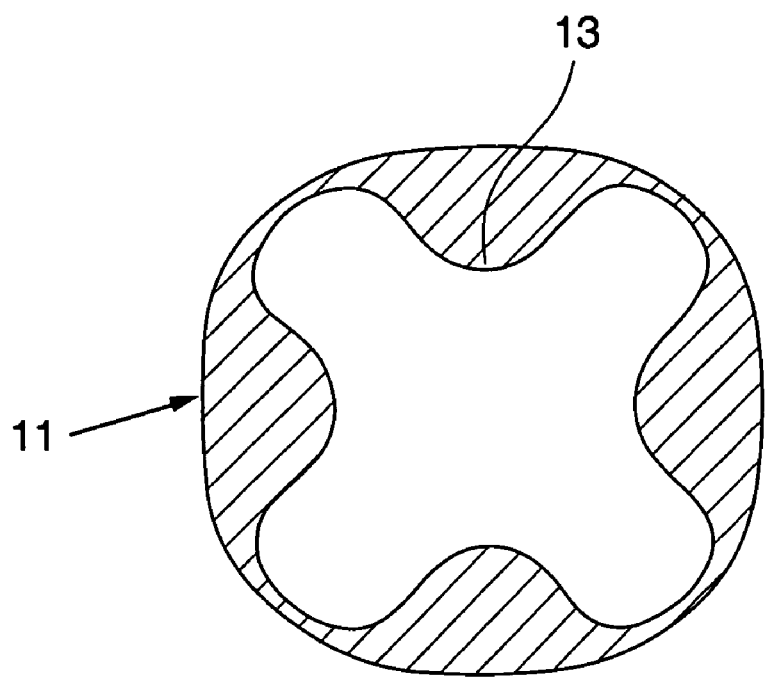
FIGS. 16A and 16B are end views of a tube for a satiation device, such as a fundal basket, antral tube, or bowel tube, illustrating tab members that may be utilized to facilitate tube removal.
Figure 16B:
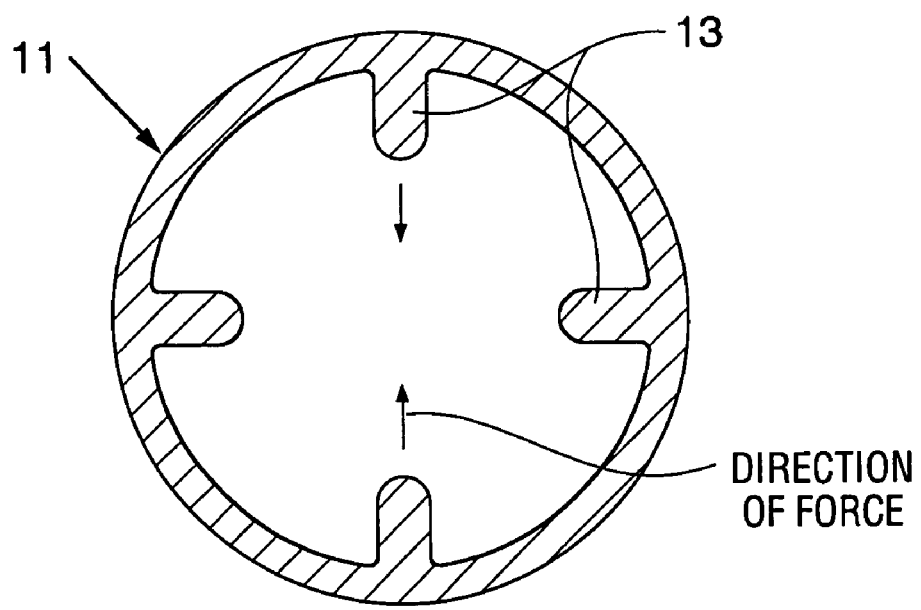

It will be appreciated that various other mechanisms may be used to facilitate collapse of the tube for removal. For example, FIGS. 16A and 16B show end views of the proximal portion of an alternative antral tube 11 which is provided to include one or more radially extending tabs 13. Tabs 13 are preferably rounded and smooth to minimize interference with flow through the tube 11. When the satiation device is to be removed, tabs 13 are drawn inwardly using endoscopic instruments, causing the tube to collapse inwardly.

Figure 5:
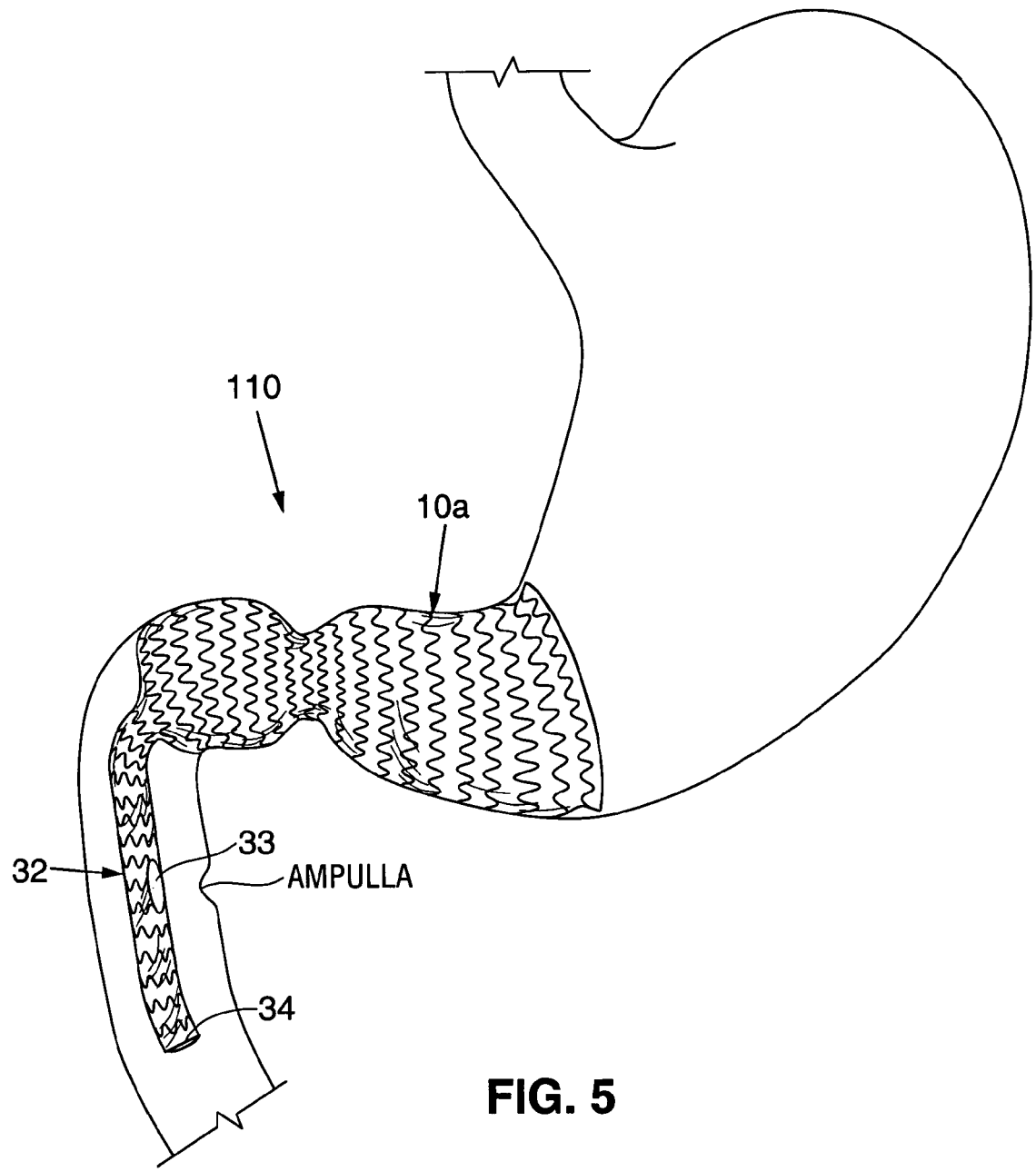
FIG. 5 is a schematic illustration similar to the illustration of FIG. 4B, showing the position of an alternative device having an antral tube and a bowel tube.

Referring to FIG. 5, an alternate embodiment of satiation device 110 includes an antral tube 10a similar to that of the previous embodiments, but additionally includes a small diameter bowel tube 32 at its distal end. The bowel tube 32 is preferably formed of a combination of mesh and polymer as described in connection with antral tube 10 of FIG. 2. It simulates a Roux en Y, or gastric bypass, procedure by keeping food away from the proximal portion of the small bowel (i.e. away from the duodenum or the jejunum and duodenum, the portions of the small intestine at which most carbohydrates and proteins are absorbed by the body). This in turn prevents absorption of food by the proximal portion of the small bowel, and thus reduces the total amount of food absorbed by the body.

The bowel tube 32 is smaller in diameter than the antral tube 10a, and is of a diameter that will allow it to press gently against the walls of the small bowel. It must also be sufficiently flexible to pass posteriorly and distally into the second portion of the duodenum without damaging the mucosa. This may be facilitated by the use of a guidewire that is first introduced with an endoscope.

The bowel tube 32 may be a soft wire mesh (formed, for example, of shape memory alloys, nitinol, stainless steel alloys, stainless steel or polymers including shape memory polymers) covered with a polymer to prevent food and digestive juices from contacting the mucosa of the duodenum. Tube 32 may be provided to have a valve 34 at its distal end, which functions to prevent reflux of intestinal contents. The bowel tube includes an opening 33 to ensure that the ampulla of vader is not obstructed.

Delivery of the device 110 into, and its removal from, the stomach may be performed under radiological or endoscopic guidance as described with respect to the prior embodiments. A conventional guide wire may also be used to facilitate positioning of the bowel tube 32. If a guide wire is used, it is first placed into the duodenum using endoscopy or radiology to guide the wire placement. The bowel tube 32 and antral tube 10a are then placed over the wire and guided over the wire into the duodenum or jejunum to the desired location. Next, the guide wire is removed. The small bowel tube position is maintained by bearing against the proximal end of the antral tube using a pushing instrument (such as the pusher 28 shown in FIG. 4A), while the covering sheath is withdrawn. As they are released from the sheath, the small bowel tube and the antral tube deploy and expand into contact with the antrum walls.

In a modular version of the device 110, the antral tube 10a and bowel tube 32 may be provided separately. Components of a modular system may be attached to one another pre-operatively or after each component has been positioned within the body.

Figure 6:
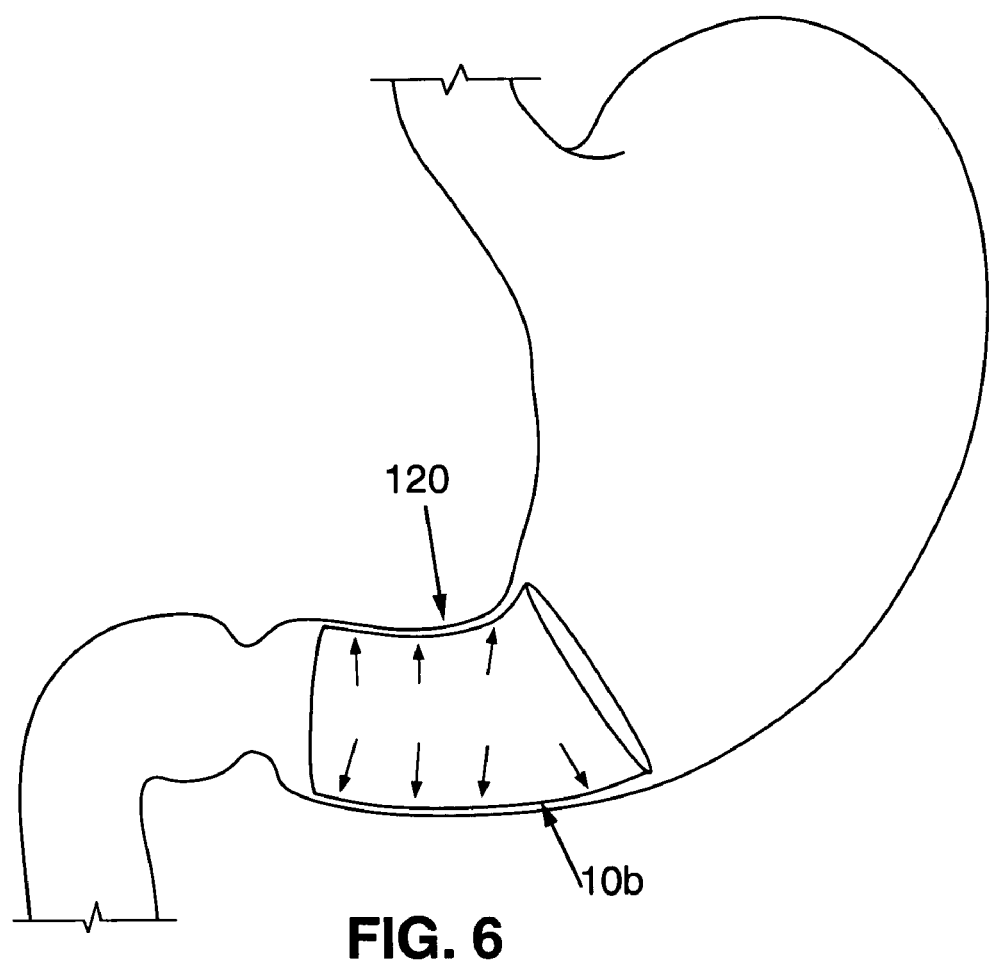
FIG. 6 is a schematic illustration similar to the illustration of FIG. 4B, showing the position of an alternative device having an antral tube that does not cross the pyloric sphincter.
Figure 7:
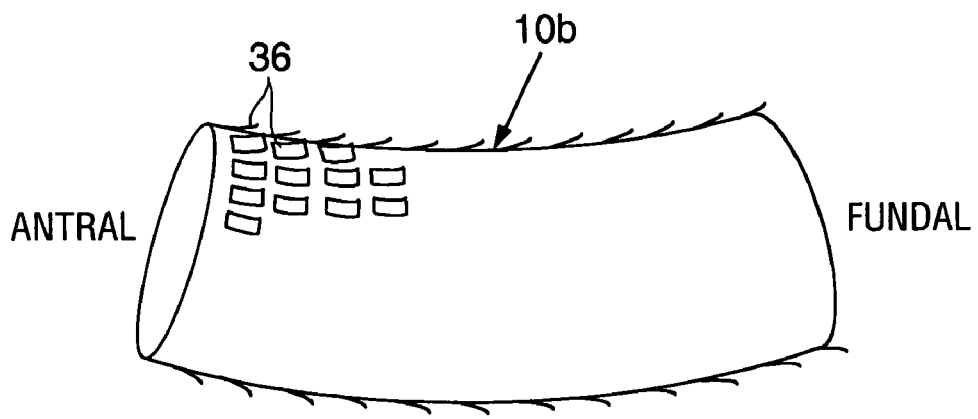
FIG. 7 is a plan view of an antral tube similar to the antral tube of FIG. 6, with retaining structures formed into the external surface.

An alternative form of a satiation device 120 may be configured, as shown in FIG. 6, to have an antral tube 10b that is positioned only within the antrum and that does not cross the pyloric sphincter. As with the prior embodiments, the satiation device 120 is preferably self-expanding and may be formed of a soft nitinol, shape memory polymer, or stainless steel mesh, preferably in combination with a polymer. Outward radial pressure between the antral tube and the stomach walls prevent the tube from moving distally through the pylorus, even in the presence of peristalsis. Additional mechanisms may be provided to prevent movement of the tube towards the fundus and/or pylorus. For example, soft and directional "fish scale" type structures 36 may be formed on the mesh or polymer on the exterior surface of the antral tube 10b as shown in FIG. 7. The figure shows the scales oriented to prevent movement of the device towards the pylorus, but it should be appreciated that movement towards the fundus may be prevented by orienting the scales in the opposite direction.

Figure 8:
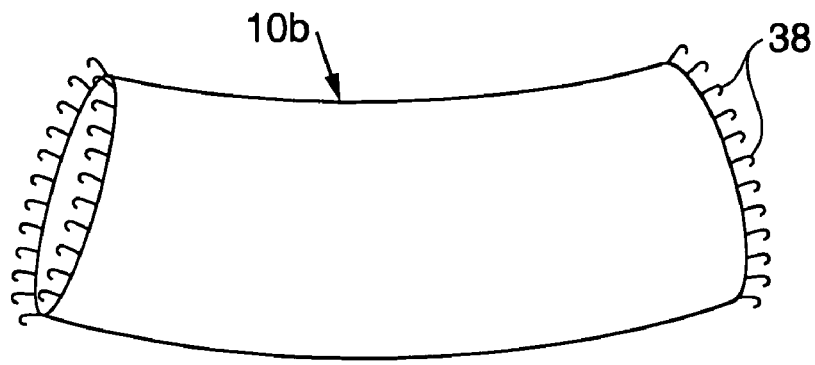
FIG. 8 is a plan view of an antral tube similar to the antral tube of FIG. 6, with retaining structures formed at the proximal and distal ends.

A plurality of hooks 38 may be formed on the proximal and/or distal ends of the antral tube 10b, as shown in FIG. 8. These hooks gently attach to the mucosa of the antrum and prevent movement in the proximal and/or distal direction. Such hooks should be sufficiently small as to not penetrate the submucosa or muscularis.

Figure 9A:
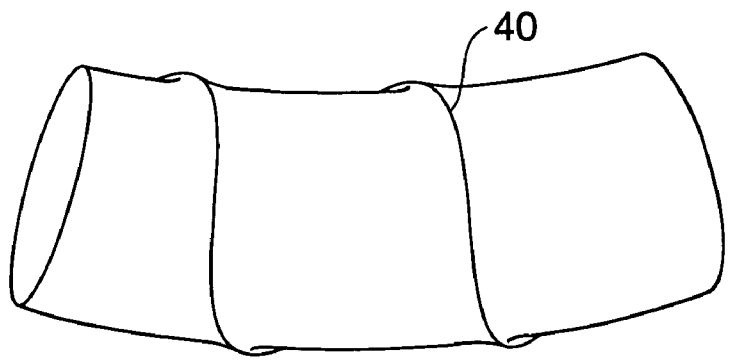
FIGS. 9A and 9B are plan views of antral tubes similar to the antral tube of FIG. 6, with variations of retaining ridges formed on their external surfaces.
Figure 9B:
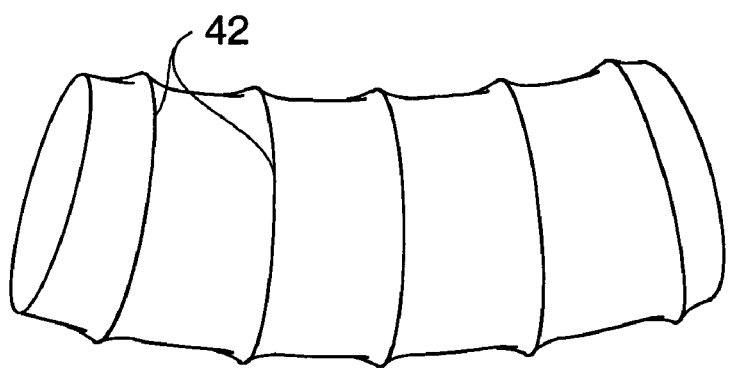

FIGS. 9A and 9B illustrate the use of ridges formed on the exterior of the antral tube for preventing migration of the tube. The ridges may be formed in a variety of configurations, such as the helical ridges 40 shown on the FIG. 9A embodiment or the rings 42 shown in the FIG. 9B embodiment. These same mechanisms for preventing movement may be applied to the bowel tube as well, as described with respect to FIGS. 10D-10F.

Figure 10A:
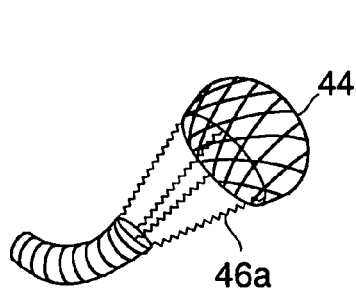
FIGS. 10A-10C are perspective views of satiation devices having antral tubes and fundal baskets.
Figure 10B:
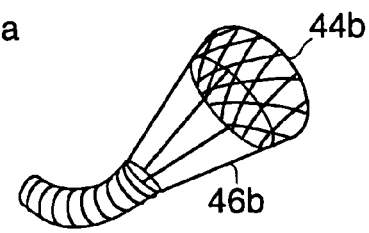
Figure 10C:
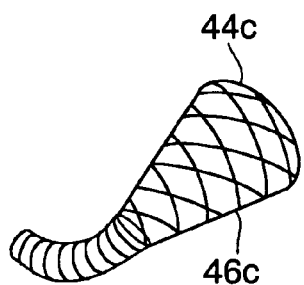

A basket structure may extend from the proximal end of the antral tube for positioning in the fundus. Referring to FIGS. 10A-10C, a fundal basket 44a, 44b, 44c may be formed of a mesh provided with large openings sized to permit food to readily flow through the fundal basket into the antral tube. Unlike the mesh of the antral tube, the mesh of the fundal basket is preferably not covered with a polymeric skin or coating. The fundal basket is mechanically connected to the antral tube, such as by spring members 46a (FIG. 10A), elongate struts 46b (FIG. 10B), mesh 46c (FIG. 10C) or equivalent structural components. The proximal end of the fundal basket rests against the walls of the fundus of the stomach and thereby functions to prevent migration of the device within the stomach. An embodiment utilizing an antral tube and fundal basket may be provided in a modular form—in which the antral and fundal components are separate from one another and then attached to one another pre-operatively or following implantation in the body. Alternatively, the antral tube and fundal basket may comprise a unitary device.

Similar attachment mechanisms may be used to attach a bowel tube to an antral tube in embodiments having these components, regardless of whether a fundal basket is used. For example, the bowel section 132b and antral section 110b may be connected with one or more longitudinal struts, as shown in FIGS. 10E and 10F. An alternative embodiment may be provided without an attachment strut, in which case bowel tube 132a may be placed separately from antral tube 110a, and it may include a neck section 133 (or tabs such as tabs 13 of FIGS. 16A/16B) at its proximal edge to allow recovery with an endoscopically controlled snare. See FIG. 10D. As discussed previously, a device of this type may be provided as a modular or unitary device.

Figure 11:
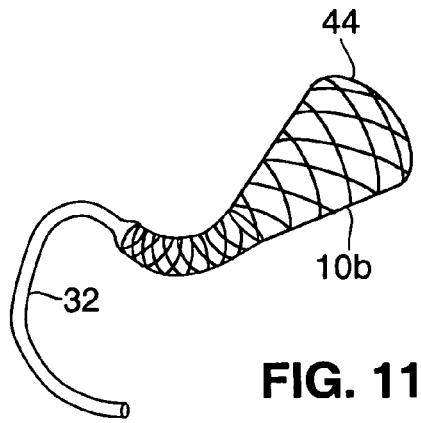
FIG. 11 is a plan view of a satiation device having an antral tube, fundal basket, and bowel tube.

Referring to FIG. 11, embodiments having an antral tube 10b and a fundal basket 44 may further include a bowel tube 32 attached to the antral tube. As discussed previously with respect to FIG. 5, the bowel tube 32 functions to keep food away from the proximal small bowel. The bowel tube 32 may have properties similar to those described with respect to the embodiment of FIG. 5.

Figure 12A:
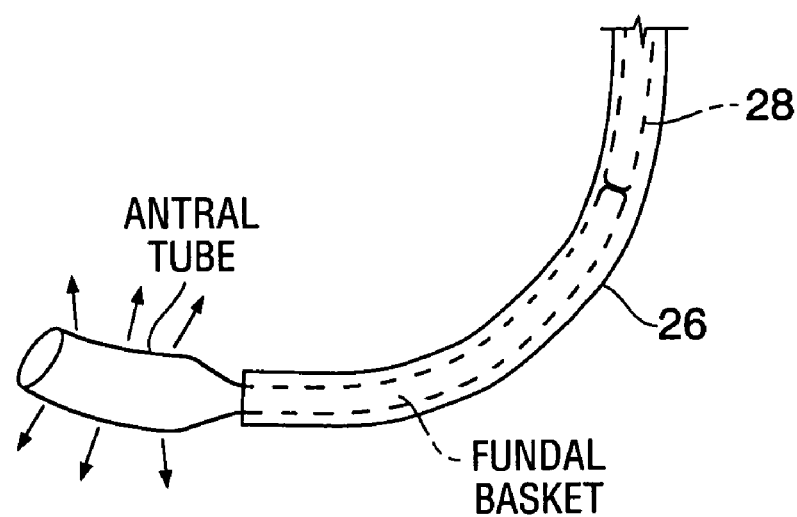
FIG. 12A is a plan view schematically illustrating insertion of a device such as the devices of FIGS. 10A-10C into the body.

As with the previous embodiment, the embodiments of FIGS. 10A-10F and 11 are preferably inserted into the stomach in a collapsed condition, such as within a sheath 26 as shown in FIG. 12A. In the case of the FIG. 10A-10C embodiments which include antral and fundal tubes only, the distal tip of the antral tube is placed at the pylorus (or across the pylorus as with the FIG. 2 embodiment) and the sheath is withdrawn. As they are released, the antral and fundal units self-expand and may shorten slightly.

Figure 10D:
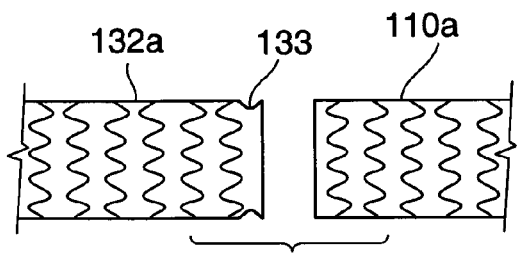
FIGS. 10D-10F are partial side elevation views of satiation devices having antral tubes and bowel tubes. Each figure illustrates a portion of the antral tube and a portion of the bowel tube.
Figure 10E:
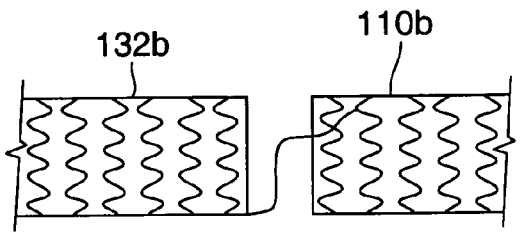
Figure 10F:
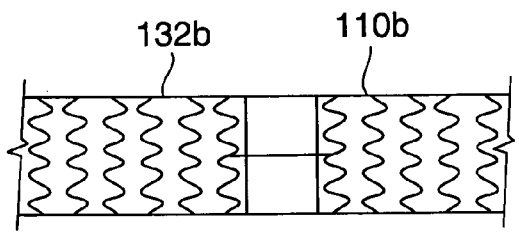

If a small bowel tube is to be included, as in FIGS. 10D-10F, the tube can be placed under radiological guidance or endoscopic guidance or over a guide wire as described above with respect to FIG. 5. As discussed, the antral tube, fundal basket and bowel tube may form parts of a unitary device, or they may be separately provided as modular components. In a modular device, each of the three components may be separately provided and then attached to one another prior to implantation or after the components have been positioned within the body. In another form of modular device, some but not all of the components (e.g. the fundal basket and antral tube, or the antral tube and bowel tube) may comprise a unitary device, and an additional modular component may be provided for subsequent attachment to the unitary device either before or after implantation.

Figure 12B:
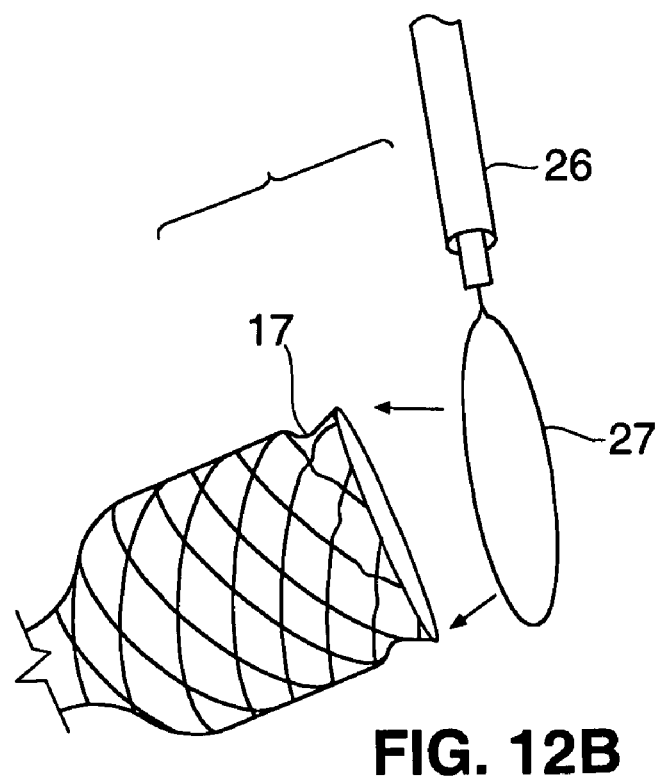
FIG. 12B is a plan view schematically illustrating removal of the device such as the devices of FIGS. 10A-10C from the body.

Referring to FIG. 12B, removing the device, whether it includes only an antral tube, fundal and antral tubes, or fundal, antral and small bowel tube, is accomplished by extending a sheath 26 into the stomach, extending a grasping instrument through the sheath, grasping the proximal end of the device and pulling the tube into the sheath causing it to collapse. If a wire snare loop is to be used as the grasping instrument, the snare is placed around a neck (such as neck 16 shown in FIG. 2 or a similar neck 17 at the proximal end of the fundal basket as shown in FIG. 12B) to grasp the device. Engagement with the snare loop would assist in collapsing the tube as the snare is tightened around the neck and withdrawn into the sheath 26. Alternatively, as described with respect to FIGS. 16A and 16B, the proximal end of the tube may include tabs 13 that are pulled radially inwardly using an endoscopic instrument to facilitate collapse of the device.

Figure 13:
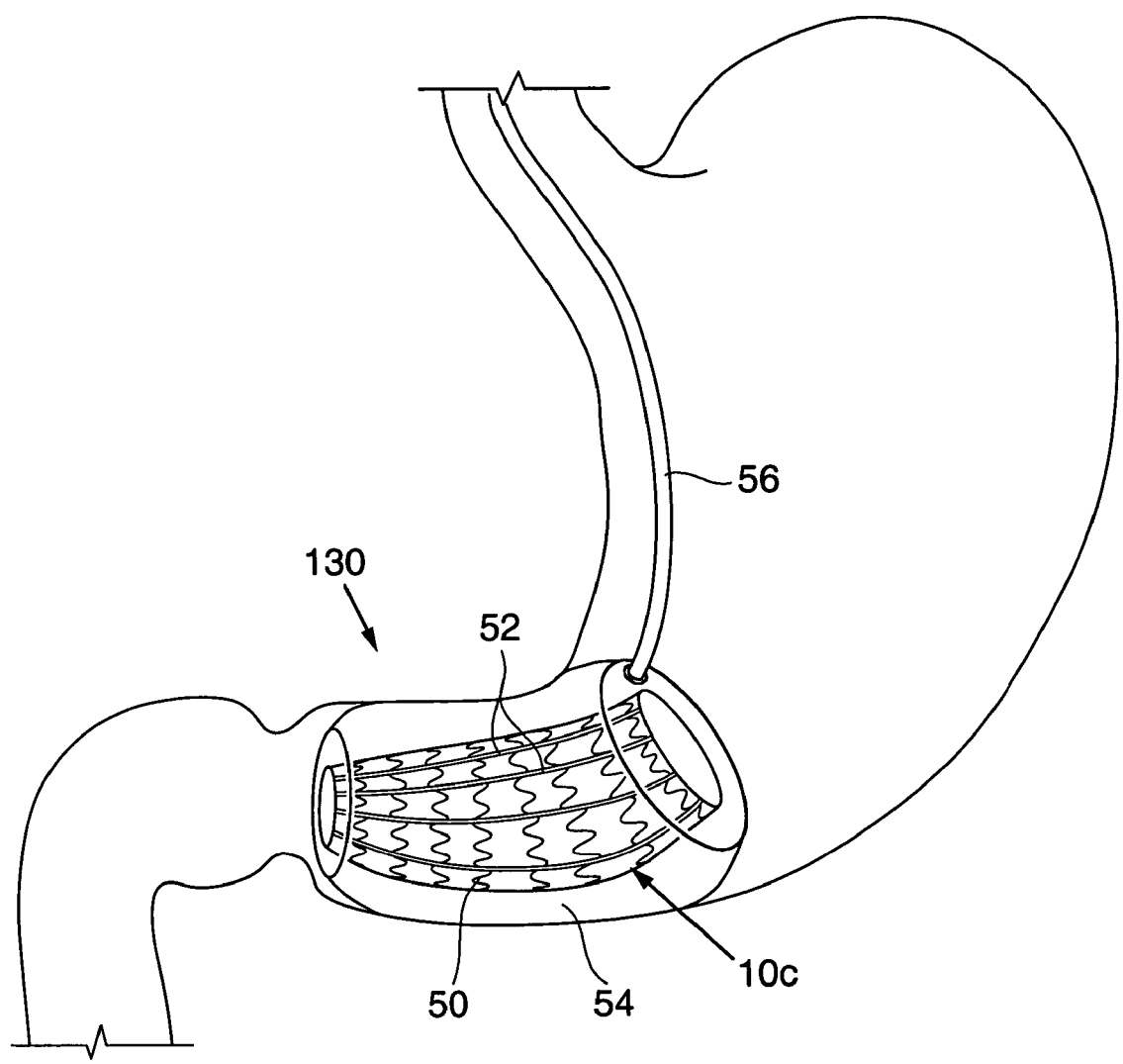
FIG. 13 schematically illustrates an alternative embodiment of a satiation device positioned within a human stomach.

Another alternative satiation device 130 is shown in FIG. 13. As with the prior devices, device 130 includes an antral tube 10c positionable within the antrum to minimize direct contact between food entering the antrum and the walls of the antrum. The antral tube 10c may be formed of a combination of soft polymeric material as well as reinforcing members formed of nitinol, stainless steel, and/or polymer. In the embodiment shown in FIG. 13, device 130 is formed of a polymeric sleeve 48 with nitinol struts 50 embedded in the sleeve material. Stainless steel or polymeric reinforcing bands 52 extend longitudinally along the interior walls of the tubular member. Inflatable reservoirs 54 formed of a soft elastic polymer are positioned on the exterior of the tubular sleeve 48. A fill tube 56 is fluidly coupled to the reservoirs. After the device is positioned within the antrum, reservoirs 54 are filled with saline to expand the sleeve 48 into contact with the antrum walls, so as to hold the device in place within the antrum. Fill tube 56 may detach from the reservoir following inflation using the saline. To prevent saline leakage, a one-way valve (not shown) may be located within the reservoir at the point of attachment of the fill tube.

Figure 14:
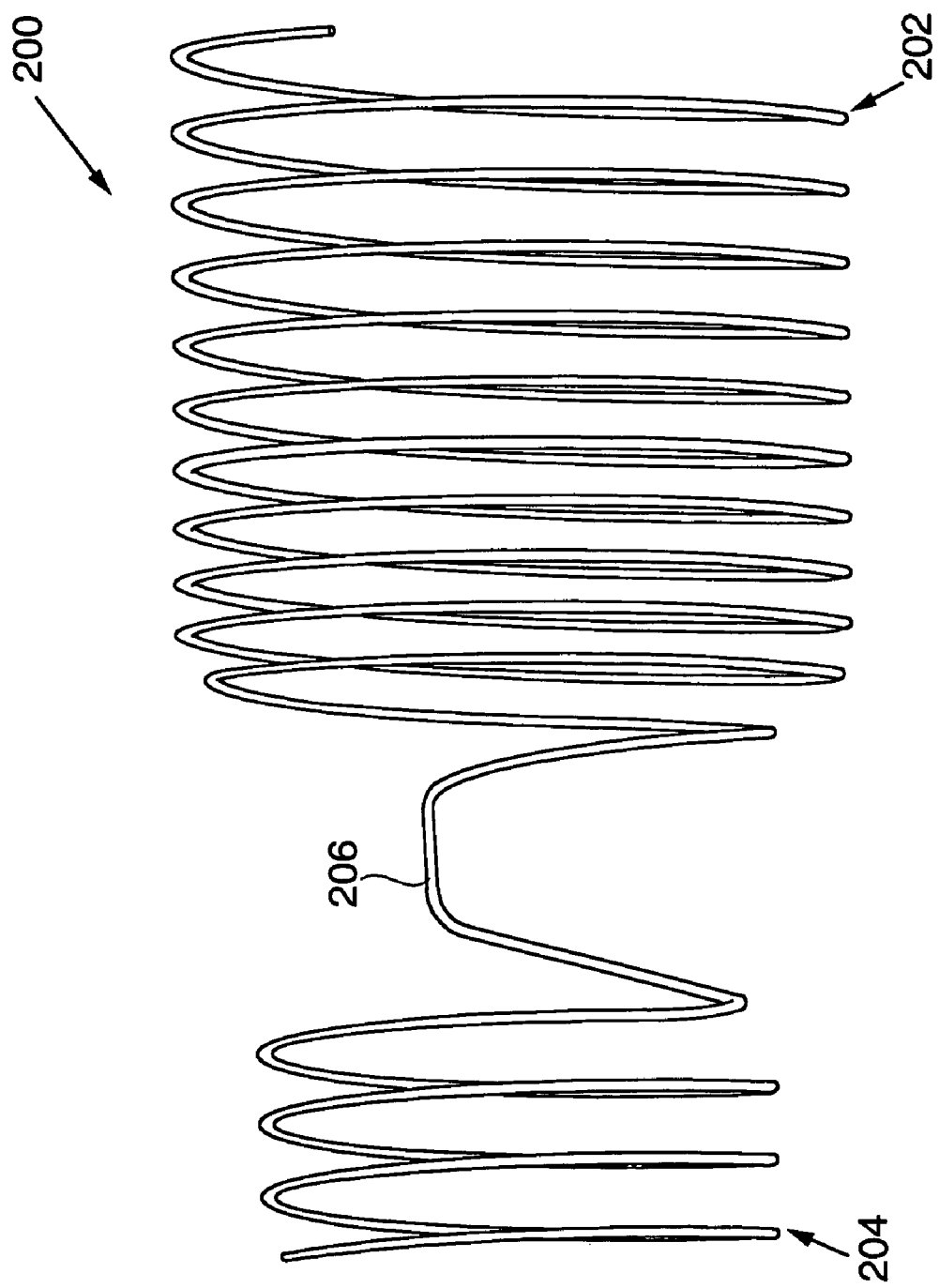
FIG. 14 is a side elevation view of a satiation device utilizing a coil configuration.
Figure 15:
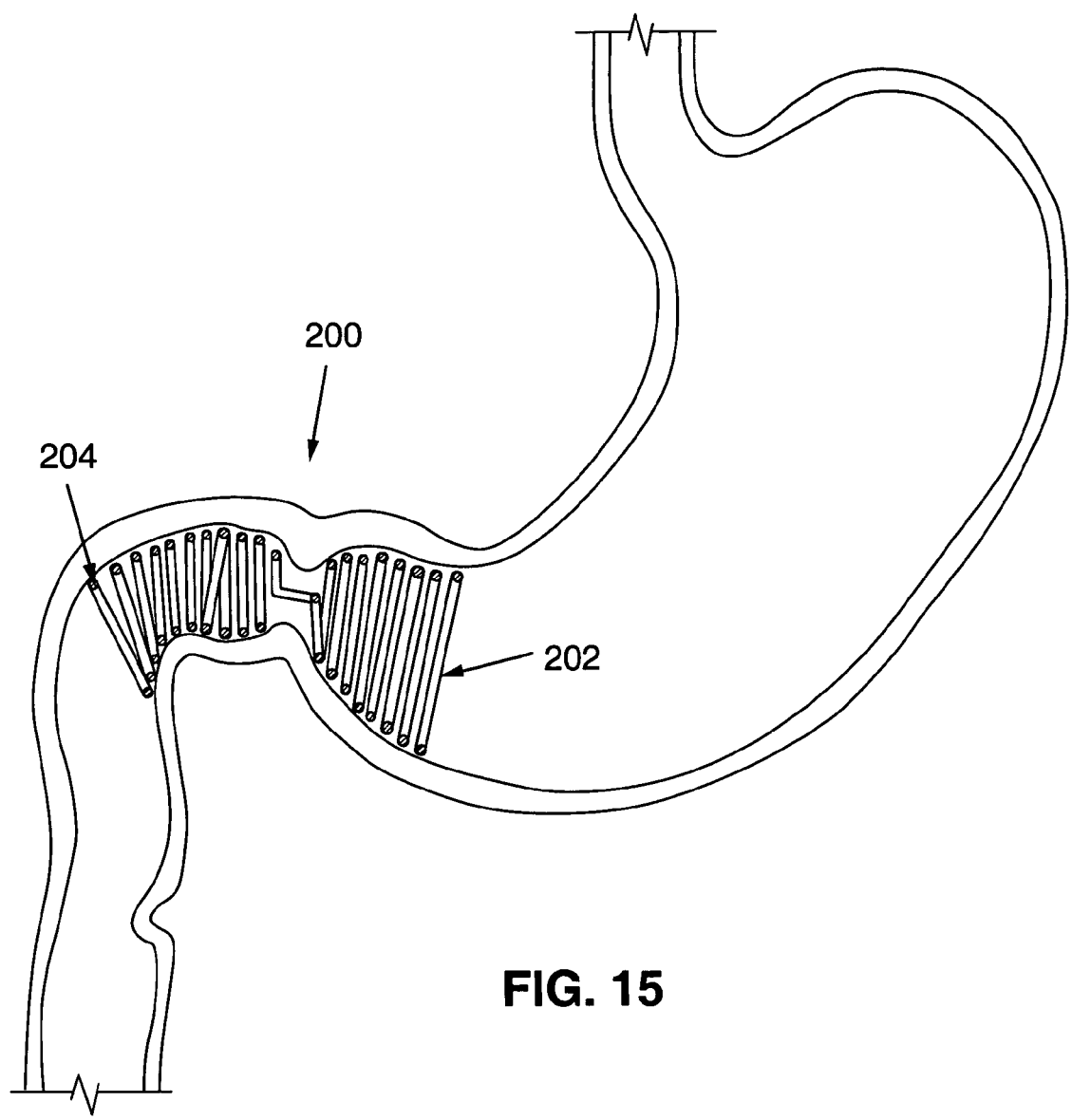
FIG. 15 schematically illustrates the satiation device of FIG. 15 positioned within a human stomach.

Another alternative embodiment of a satiation device 200 is shown in FIGS. 14 and 15. Device may be formed of a wire member coiled to create a stent-like device. The coil may be contoured to match the contours of interior lumen wall, such as by forming the coil of a shape memory material such as nitinol or polymers, and shape setting the material to the desired shape. Device 200 has a proximal portion 202 positionable in the antrum, and a distal portion 204 that may be positioned in the duodenum bulb or further within the small intestine. The pitch of the coil is selected to give the device 200 a desired strength and flexibility.

A straight portion 206 connects the proximal and distal portions 202, 204. Straight portion 206 is positionable within the pyloric sphincter. Under normal conditions, the pyloric sphincter remains closed until the stomach is ready to evacuate its contents into the duodenum. Straight portion 206 is beneficial in that it provides structure connecting proximal and distal portions 202, 204 while allowing the pyloric sphincter to correctly perform its normal function.

Although a preferred material for the device 200 is wire, it should be noted that a variety of alternative materials may be used for this purpose. For example, device 200 may be formed of ribbons of material, or it may be formed from a metallic sheet, or its pattern may be cut from tubing.

Figure 17A:
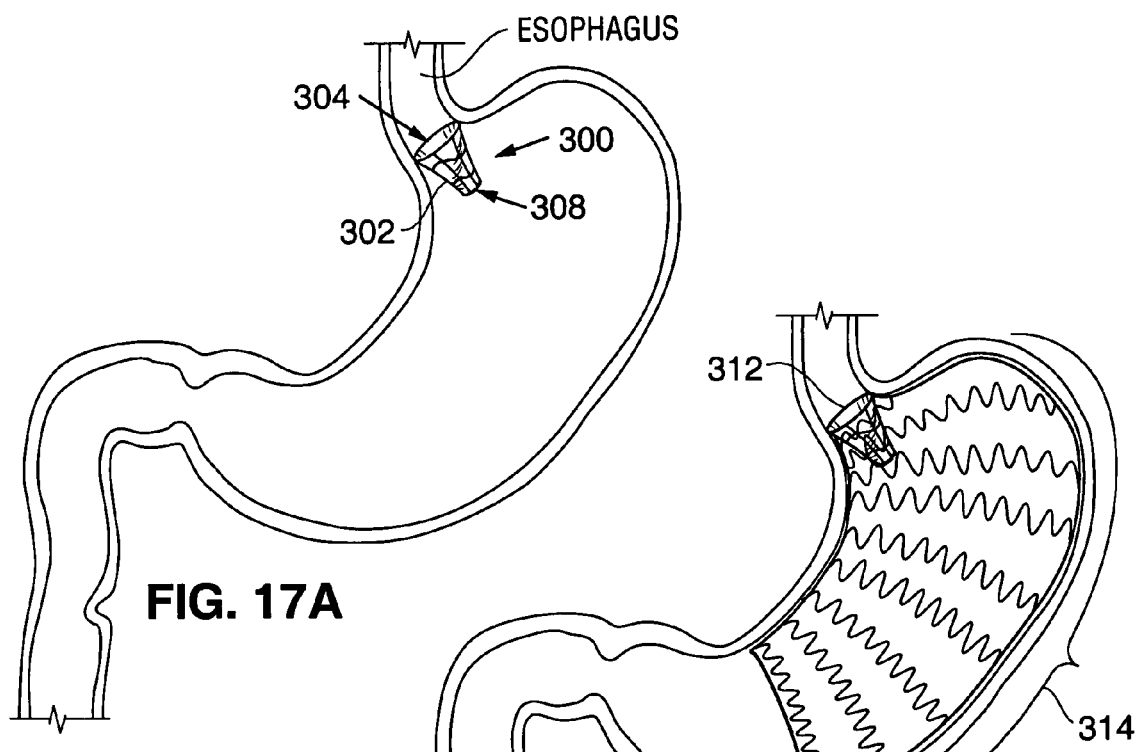
FIG. 17A schematically illustrates in vivo positioning of an alternative satiation device utilizing a standalone stomach pouch.

Yet another embodiment of a satiation device 300 is illustrated in FIG. 17A. Device 300 includes a tubular pouch 302 that is positioned in the proximal region of the stomach. Pouch 302 includes a proximal end that is preferably positioned to be slightly proximal of the gastro_o-esophageal junction as shown. The walls of the pouch preferably taper inwardly from the proximal end towards the distal end. A proximal opening 304 of, for example, approximately 25 to 50 mm in diameter is located at the proximal end, and a distal opening 308 having a diameter of approximately 6-12 mm is formed at the distal end. The proximal opening 304 is preferably placed into alignment with the esophagus, and the distal opening 308 opens into the interior of the stomach.

Because of its small volume (which may be on the order of approximately 30cc-50cc in volume), the pouch functions to limit the amount of food that can be consumed at one time. Food ingested by the patient remains in the pouch until digestive enzymes have broken it down sufficiently for it to pass through the distal opening 308.

The pouch is preferably self-expanding and may take a variety of forms. For example, referring to FIG. 18 it may be formed of struts 310 or a mesh formed of nitinol, stainless steel, polymer (including shape memory polymer). A ring 312 is attached to the struts/mesh at the proximal end of the device, and also may be formed of nitinol, stainless steel, polymer (including shape memory polymer). The exterior or interior of the pouch covered with a material 313 will prevent passage of food through the sides of the pouch. One example of such a material is a polyester material such as the polyester sold by the DuPont Company under the trademark Dacron.

Figure 19A:
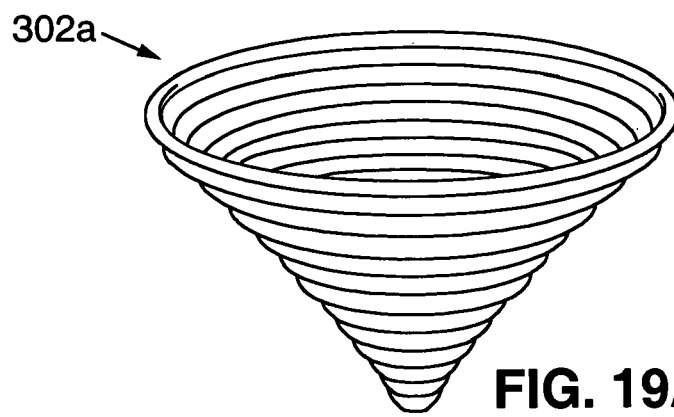
FIG. 19A is a perspective view of an alternative stomach pouch of a type that may be utilized as shown in FIGS. 17A-17C.
Figure 19B:
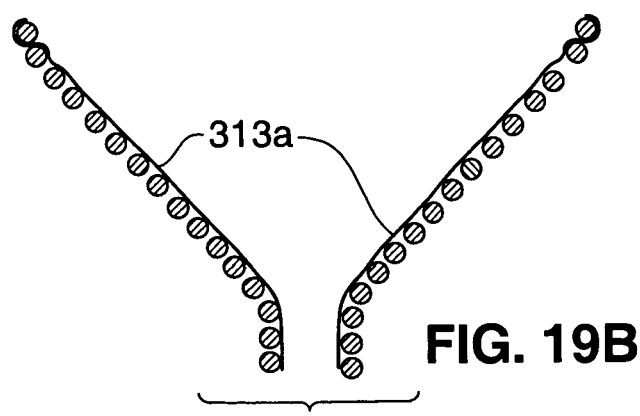
FIG. 19B is a cross-sectional side view of the stomach pouch of FIG. 19A.

FIGS. 19A and 19B show another example of a pouch 302a. Pouch 302a is formed of a shape memory coil that has been heat set to a funnel shape. Dacron polyester or other material 313a (FIG. 19B) may optionally cover the interior or exterior walls of the coil, although the coil may itself be sufficiently small as to prevent migration of food to the surrounding stomach walls. The material 313a may be pinched between proximal-most coil 312a and its adjacent coil as shown in FIG. 19B, so as to hold it in place.

Figure 18:
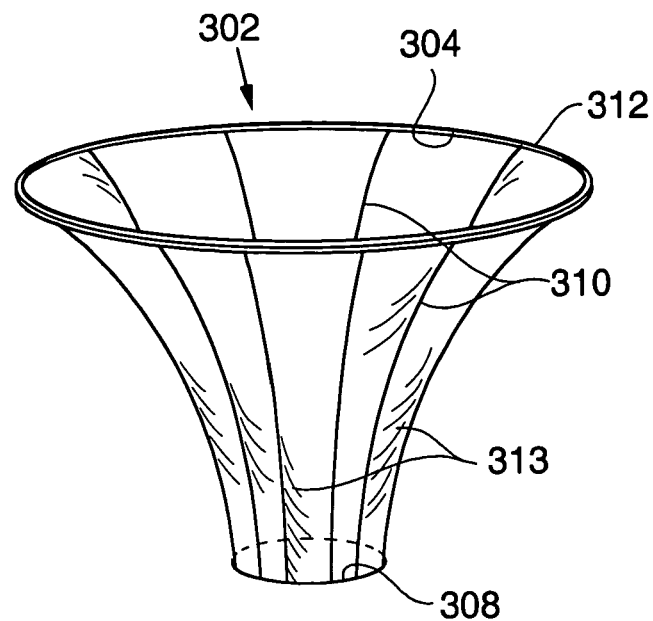
FIG. 18 is a perspective view of a stomach pouch of a type that may be utilized as shown in FIGS. 17A-17C.

The pouches 302, 302a may be provided with a proximal-to-distal dimension that is fairly long (e.g. on the order of approximately 2.5-5.0 cm) and that thus gives the pouch a funnel shape as shown in FIGS. 18 and 19A. However, a variety of alternative shapes may be used for the pouch. For example, the pouch may have a much shorter proximal-to-distal dimension and thus take the shape of a shallow saucer with a small hole on its bottom surface.

The stomach pouch may be used alone or in combination with other components. If used without additional components, the proximal end of the pouch (e.g. ring 312 of pouch 302 or ring 312a of pouch 302a) may serve as a sewing ring that is attached by sutures to the interior stomach walls. The suture may pass through the material 313, 313a (see FIG.

19B) to strengthen the connection between the stomach wall and the device. Alternatively, the pouch may be used as a standalone device without sutures—in which case it may be held in place by the radial expansion forces of the struts, mesh or coils.

Figure 17B:
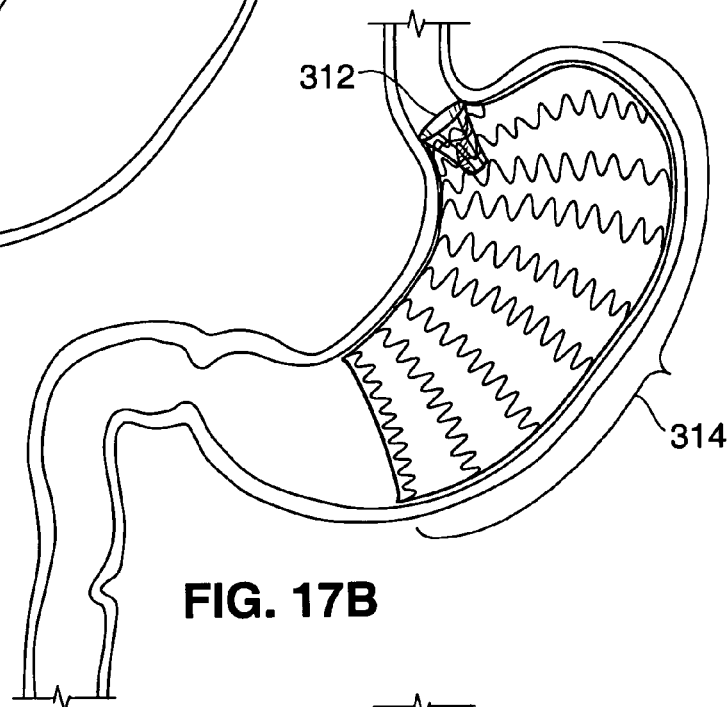
FIG. 17B is a schematic illustration similar to FIG. 17A, but further illustrating a cage in combination with the stomach pouch.

The stomach pouch may alternatively be one portion of a larger satiation device. For example, referring to FIG. 17B, the proximal portion of the pouch (such as ring 312 of the pouch of FIG. 18 or the upper coil 312a of the pouch of FIG. 19A) may be connected to the proximal end of a larger cage structure 314. Cage 314 extends from the esophagus to the proximal portion of the antrum, and may be similar to the fundal baskets described above. It may be a large stent-like structure preferably formed of self-expanding material, such as stainless steel or a shape memory material such as nitinol or polymer. Cage 314 functions primarily to distend the stomach to create a feeling of satiety. As shown, the pouch 300 is suspended into the interior of cage 314.

Figure 17C:
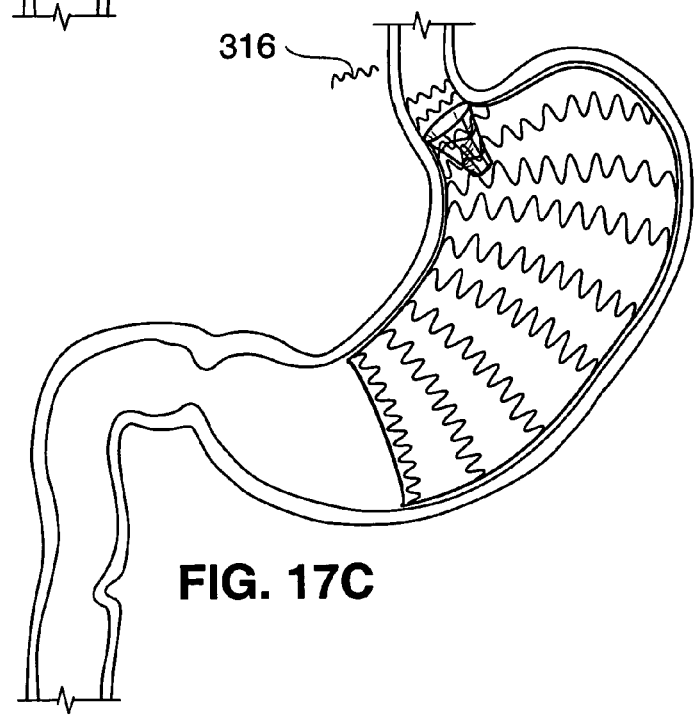
FIG. 17C is a schematic illustration similar to FIG. 17B, but further illustrating an alignment extension in combination with the stomach pouch and cage.

Additionally, the pouch (as used with or without cage 314) may also be attached at its proximal end to an alignment extension 316. Referring to FIG. 17C, alignment extension 316 is a tubular stent portion that extends into the esophagus. In one embodiment, extension 316 may be approximately 5 cm in length. It functions primarily to keep the proximal opening of the pouch aligned with the esophagus—so that food passing through the esophagus passes easily into the pouch.

Figure 17D:
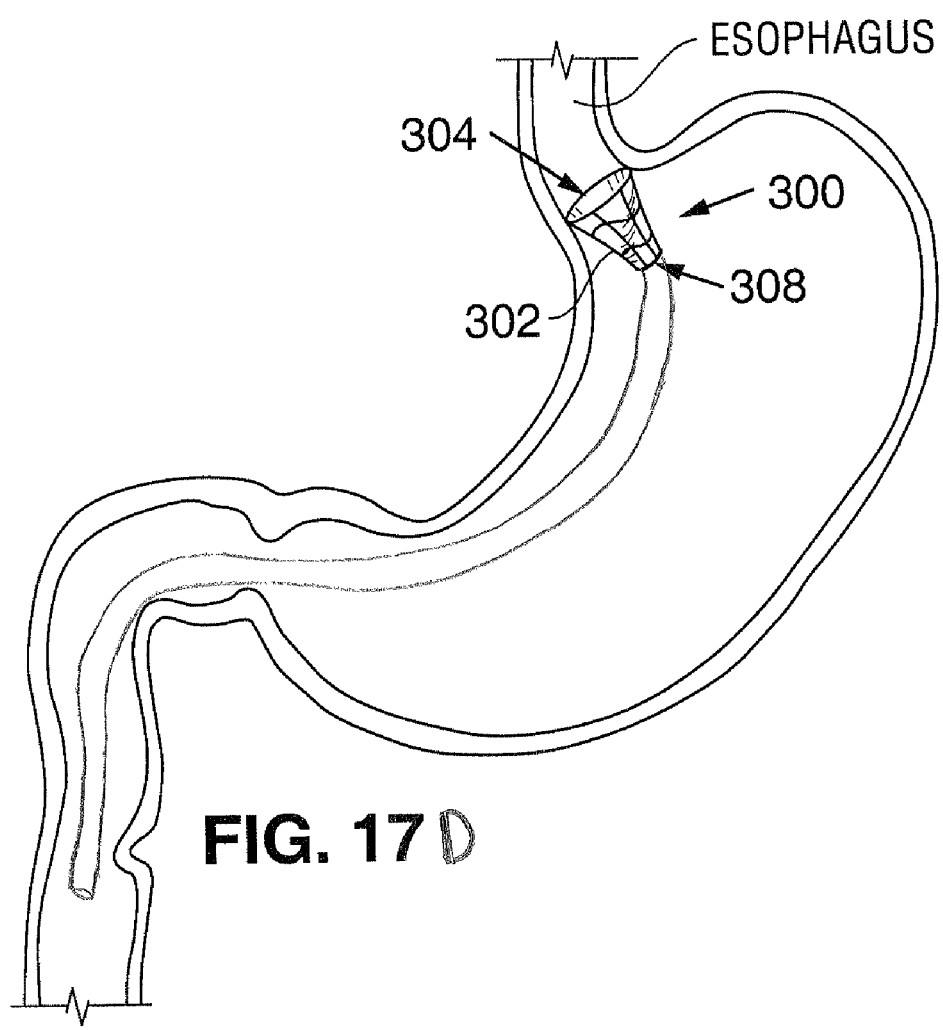
FIG. 17D is a schematic illustration similar to FIG. 17B, but further illustrating a bypass tail in combination with the pouch.

Finally, an enclosed bypass tail may extend from distal opening 308 of the pouch through the pylorus into the small bowel, as shown in FIG. 17D, to simulate a stomach bypass procedure. The structure of the tail maybe similar to the bowel tube described with respect to FIG. 5.

The stomach pouch and associated components may be implanted and removed using procedures of the type described with respect to previous embodiments. In embodiments in which the stomach pouch includes the cage, alignment extension, and/or bypass tail, the components may be implanted simultaneously as a single device. Alternatively, they may be segmented for separate implantation and for subsequent suture attachment to one another once they are within the body.

Figure 20:
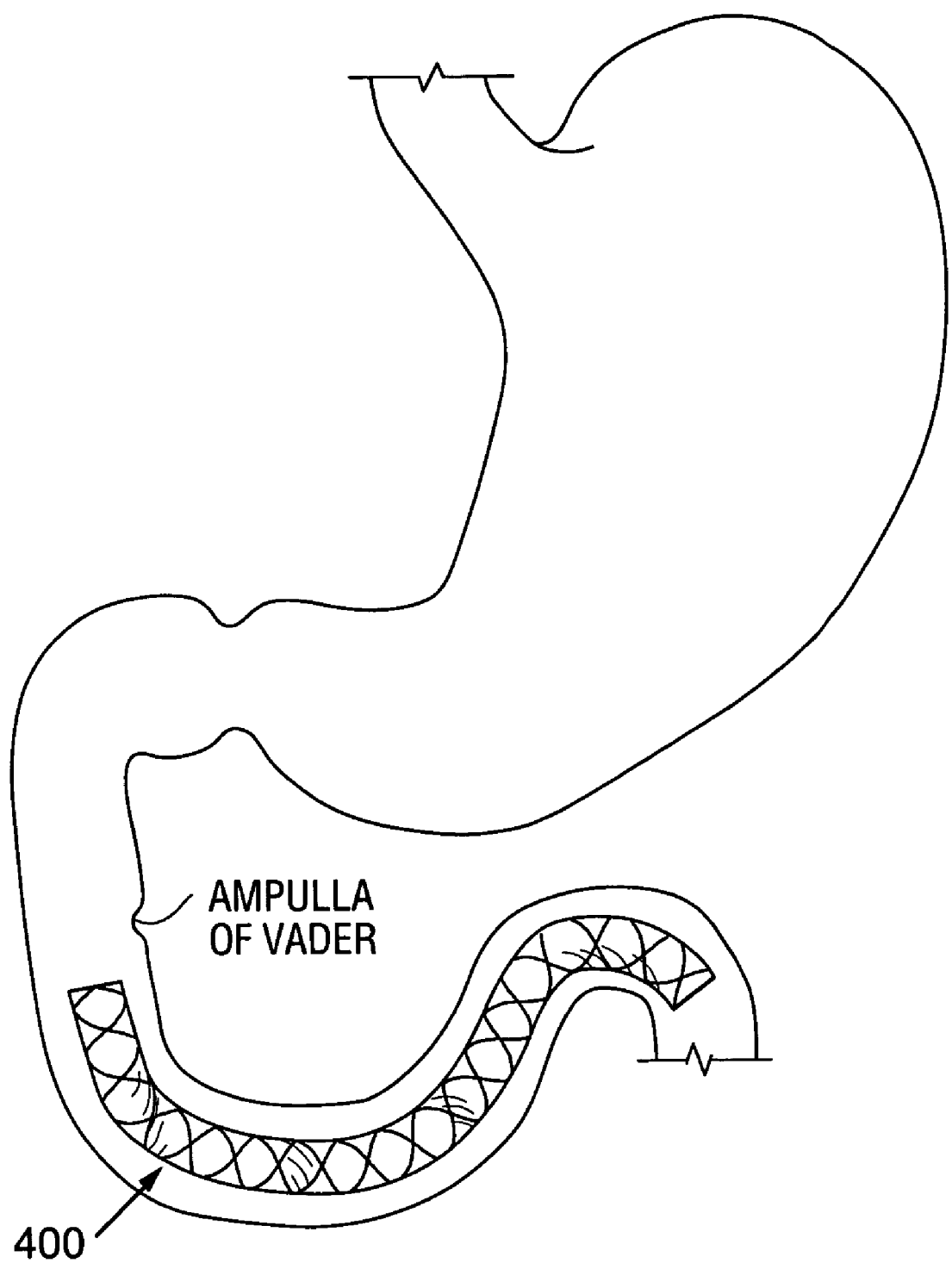
FIG. 20 illustrates in vivo positioning of an alternative satiation device utilizing a duodenal absorption barrier prosthesis.

Another embodiment of a satiation device is illustrated in FIG. 20. This satiation device includes a duodenal absorption barrier—an elongate tube 400 that is positionable within the small intestine at a location slightly distal of the ampulla of vader. For example, the barrier may be positioned a distance of approximately 1 cm or more from the ampulla of vader. Positioning of the tube so that it does not contact the ampulla (an opening through which bile passes into the duodenum) is desirable in that it minimizes the chance of irritation and choleocystitus.

The tube 400 is preferably a flexible tube preferably approximately 20 cm or more in length. It may be constructed as described with the satiation devices described above. For example, it may be formed of a self-expandable material such as nitinol, stainless steel, or a shape memory polymer (e.g. oligo-(caprolactone)-dimethacrylate or n-butyl acrylate), and covered with a polymer covering that is resistant to gastric juices (e.g. silicone) and that prevents passage of food byproducts through the walls of the tube.

The tube 400 prevents caloric intake in the small intestine by preventing absorption of food through the walls of the duodenum, and thus functions as an aid to weight loss.

Tube 400 may be delivered and extracted using the techniques described above, and it may be held in place in any of the ways described herein, including sutures, barbs, scales, hooks, or under the outward pressure of the expanded device against the surrounding walls of the duodenum. Tube 400 may be used alone or in combination with components of the type described above.

Various embodiments of satiation device have been described herein. These embodiments are giving by way of example and are not intended to limit the scope of the present invention. It should be appreciated, moreover, that the various features of the embodiments that have been described may be combined in various ways to produce numerous additional embodiments.

We claim:

1. A method of inducing weight loss in a patient having an esophagus, a stomach, and an intestine, the method comprising the steps of:
   passing in a distal direction an obesity-controlling prosthesis through the esophagus and into the stomach, the prosthesis comprising an elongate sleeve having an upstream opening and a downstream opening;
   coupling the prosthesis within the stomach with the upstream opening in the proximal stomach; and
   positioning the downstream opening within the intestine.

2. The method of claim 1, wherein food ingested by the patient passes from the esophagus into the sleeve, and flows from the sleeve into the intestine.

3. The method of claim 1, wherein the sleeve includes an upstream component having the upstream opening and a downstream component having the downstream opening, and wherein the method includes coupling the upstream and the downstream components to one another after passing them through the esophagus.

4. The method of claim 1, wherein the upstream opening is proportioned to restrict the rate at which food flows from the esophagus into the upstream opening.

5. The method of claim 1, wherein a proximal portion of the sleeve is tapered to form a proximal pouch.

6. The method of claim 1, wherein the sleeve comprises a polymeric material.

7. The method of claim 6, wherein the sleeve further comprises a mesh material having the polymeric material thereon.

8. The method of claim 1, wherein the sleeve includes a sidewall and a lateral opening in the sidewall.

9. The method of claim 8, wherein the positioning step includes positioning the lateral opening adjacent the ampulla vader.

10. The method according to claim 1, wherein the retaining step retains the prosthesis in the absence of fasteners coupled to the prosthesis and piercing stomach tissue.

11. The method according to claim 10, wherein the prosthesis includes an expandable framework, and wherein the retaining step includes the step of introducing the framework into the stomach in a collapsed position and expanding the framework into contact with the stomach wall.

12. The method according to claim 1 wherein the prosthesis is retained with the upstream opening in the gastro-esophageal junction of the stomach.

13. The method according to claim 1, wherein coupling the prosthesis includes coupling the prosthesis to tissue of the gastro-esophageal junction.

14. The method according to claim 1, wherein the prosthesis is proportioned to restrict the rate at which food flows from a proximal to a distal direction.

* * * * *